United States Patent [19]

Sircar

[11] Patent Number: 4,656,170

[45] Date of Patent: Apr. 7, 1987

[54] N-[4-[2-(1,4,5,6-TETRAHYDRO-4-METHYL-6-OXO-3-PYRIDAZINYL)ETHENYL]PHENYL]ACETAMIDE AND RELATED COMPOUNDS

[75] Inventor: Ila Sircar, Ann Arbor, Mich.

[73] Assignee: Warner-Lambert Company, Morris Plains, N.J.

[21] Appl. No.: 737,741

[22] Filed: May 28, 1985

[51] Int. Cl.[4] .................... A61K 31/50; C07D 237/04; C07D 237/14
[52] U.S. Cl. .................................. 514/247; 544/239; 562/433
[58] Field of Search .......................... 544/239; 514/247

[56] References Cited

U.S. PATENT DOCUMENTS

| 3,746,712 | 7/1973 | Ross | 544/239 |
| 4,353,905 | 10/1982 | Sircar et al. | 544/239 |
| 4,508,721 | 4/1985 | Hargreaves | 544/239 |

OTHER PUBLICATIONS

Derwent for EP 81,906.

Primary Examiner—Mark L. Berch
Attorney, Agent, or Firm—Joan Thierstein

[57] ABSTRACT

The present invention relates to N-[4-[2-(1,4,5,6-tetrahydro-4-methyl-6-oxo-3-pyridazinyl)ethenyl]phenyl]acetamide and their derivative compounds which have valuable pharmacological properties and in particular cardiotonic, antihypertensive, and antithrombotic activities.

9 Claims, No Drawings

N-[4-[2-(1,4,5,6-TETRAHYDRO-4-METHYL-6-OXO-3-PYRIDAZINYL)ETHENYL]PHENYL]ACETAMIDE AND RELATED COMPOUNDS

BACKGROUND OF THE INVENTION

6-Pyridylvinylpyridazine-3(2H)-one and the 4,5-dihydro compound have been described as having cardiotonic and/or antihypertensive activity in European Patent Application No. 81,906. 4,5-Dihydro-6-[2-[4-(1H-imidazol-1-yl)phenyl]ethenyl]-3 (2H)-pyridazinones are the subject of U.S. application Ser. No. 669,323 filed Nov. 9, 1984 now U.S. Pat. No. 4,599,332, which is equivalent to EP No. 84308465.8 filed Dec. 6, 1984. The present invention differs in that it does not include an imidazolyl substituent and, theretore, is not taught by EP No. 84308465.8 which additionally is not yet published.

Other pyridazinone type compounds are taught in the U.S. application Ser. No. 477,695 filed Mar. 22, 1983, and U.S. application Ser. No. 685,640 filed Dec. 24, 1984, and U.S. Pat. No. 4,353,905 issued Oct. 12, 1982. U.S. Pat. No. 4,353,905 includes an imidazolyl substituent but does not teach the alkenylene bridge of the present invention. None of the aoove references include a combination of pyridazinone substituents of the present invention.

SUMMARY OF THE INVENTION

The present invention relates to N-[4-[2-(1,4,5,6-tetrahydro-4-methyl-6-oxo-3-pyridazinyl)ethenyl]-phenyl]acetamide and derivatives having valuable pharmacological properties and in particular cardiotonic, antihypertensive, and antithrombotic activities.

Accordingly, the present invention is a compound of the formula

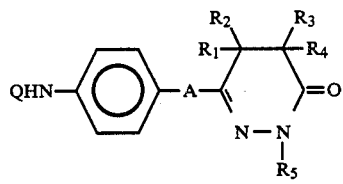

wherein Q is H or $COR_6$ wherein $R_6$ is lower alkyl of from one to four carbons inclusive or aryl; $R_1$, $R_2$, $R_3$, $R_4$, and $R_5$ are each independently hydrogen, lower alkyl or $R_2$ and $R_3$ when taken together may form a single bond such that a double bond is formed between the carbons to which $R_2$ and $R_3$ are attached. A is alkylene of one to four carbon atoms or alkenylene of two to four carbon atoms, or a pharmaceutically acceptable acid addition salt thereof; as well as a pharmaceutical composition comprising an effective amount of a compound of Formula I together with a pharmaceutically acceptable carrier; a process for preparing the compound of Formula I; a method for increasing cardiac contractility in a mammal in need thereof which comprises administering to said mammal an effective amount of a pharmaceutical composition containing a compound of Formula I, and a method of lowering blood pressure in a mammal suffering from hypertension and the prophylaxis and therapy of thromboembolistic diseases which comprises administering to said mammal an effective amount of a pharmaceutical composition containing a compound of Formula I.

DETAILED DESCRIPTION

The term "alkylene of one to four carbon atoms" refers to a straight or branched hydrocarbon chain bonded at each end to other groups and is, for example, ethylene, 1-methylethylene, propylene, butylene, 1-methylpropylene, 2-methylpropylene, or 1,1-dimethylethylene.

The term "alkenylene of two to four carbon atoms" refers to a straight or branched hydrocarbon chain containing a double bond and bonded to other groups at each end and is, for example, ethenylene, allylene, 1-methylethenylene, 3-methyl-1-propenylene, 1-butenylene, 2-butenylene, 2-methyl-1-propenylene, and the like.

The term lower alkyl is methyl, ethyl, propyl, butyl, or isomers thereof.

The term aryl is phenyl optionally substituted by one or more of alkyl of from one to four carbons, inclusive; halo; nitro; amino; mono- or di-alkylamino wherein the alkyls together are from one to six carbons, inclusive; cyano; lower alkoxy of from one to four carbons, inclusive; lower thioalkyl of from one to four carbons, inclusive; or heteroaryls.

Heteroaryls include one to three nitrogen in the ring such as pyridyl, primidinyl, or triazolyl and the like.

The compounds of Formula I are useful both in the free base form and in the form of acid addition salts when appropriate. For example compounds of Formula I wherein Q is phenyl substituted by amino, mono- or di-alkyl amino, or a heteroaryl may form such salts. Both forms are within the scope of the invention. The acid addition salts are a more convenient form for use; and in practice, use of the salt form amounts to use of the base form. In practicing the invention, it was found convenient to form the sulfate, phosphate, or methanesulfonate salts. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compound of Formula I where $R_5$ is hydrogen and $R_2$ and $R_3$ form a double bond as described above may exist in tautomeric forms, that is, as formula II or as Formula IIA as follows:

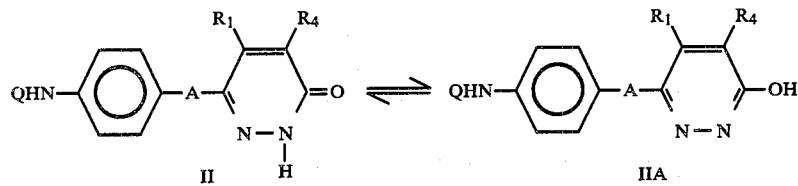

The most preferred embodiment of the present inventions is a compound of the Formula 1 wherein A is ethenyl and Q is C(O)CH$_3$, R$_1$ is CH$_3$, and R$_2$—R$_5$ are H so the compound is N-[4-[2-(1,4,5,6-tetrahydro-4-methyl-6-oxo-3-pyridazinyl)ethenyl]phenyl]acetamide.

The compounds of Formula 1 may be prepared by a process which comprises reacting a compound of the formula

with a compound of the formula

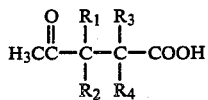

wherein Q, is COCH$_3$ and R$_1$, R$_2$, R$_3$, and R$_4$ have been defined above, in solvent or mixture of solvents, such as toluene or toluene/THF in the presence of piperidine to produce a compound of the formula

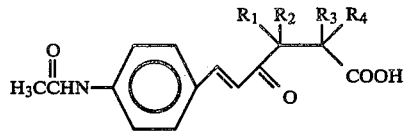

and then the compound of the formula V is treated with hydrazine hydrate (optionally substituted by lower alkyl) denoted hereinafter as R$_5$—NHNH$_2$ in 85% acetic acid to obtain the compound of the Formula I$_1$.

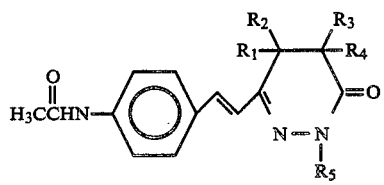

Compounds of Formula I where Q is other than COCH$_3$ is obtained by hydrolysis and reacting the resultant product with Q$_2$O wherein Q is other than COCH$_3$ to give the requisite compound.

When desired, the compound of Formula I wherein A is alkylene of one to four carbon atoms is converted to a compound of the formula

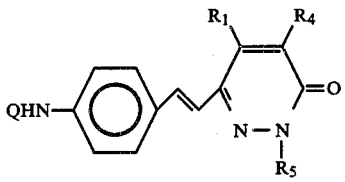

with an oxidizing agent such as manganese dioxide or m-nitrobenzenesulfonic acid according to a procedure described by W. V. Curran and A. Ross in *J. Med. Chem.*, 17, 273 (1974).

The compounds of Formula IV used as starting materials are known or, if new, may be prepared by known means.

The following schematic diagram illustrates by way of example the preparation of a compound of Formula I, wherein R$_1$ and R$_2$ are either H or lower alkyl.

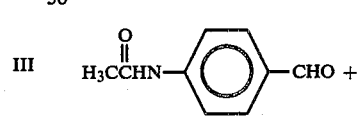

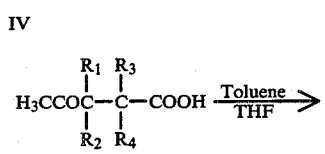

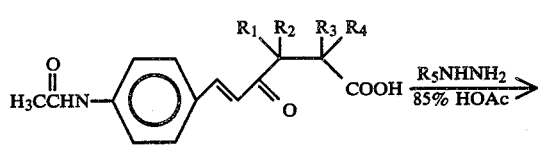

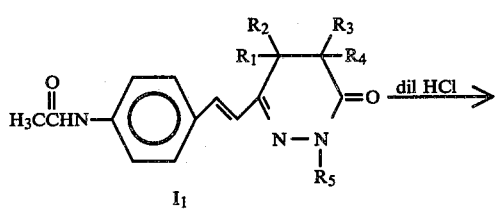

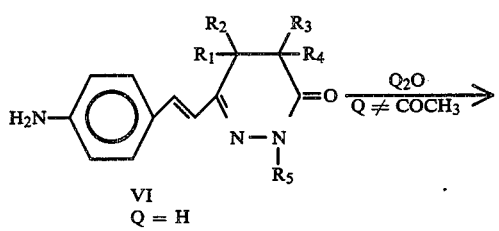

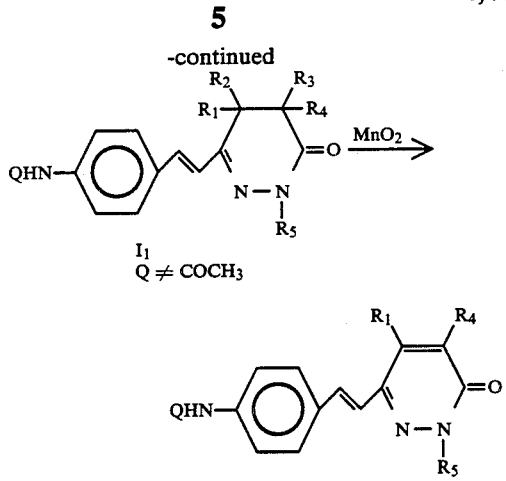

Alternatively, compounds of Formula IV wherein the $CH_3C(O)-$ group in $R_6C(O)-$ wherein $R_6$ is other than methyl are known or can be readily prepared by methods known in the art to be used in the above schematic diagram to prepare analogous compounds having the $R_6C(O)-$ group.

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

Test For In Vivo Myocardial Inotropic Activity In Anesthetized Dog

This screen consists of determining the effects of increasing intravenous doses of compound on myocardial contractility (dP/dt max of left ventricular blood pressure), heart rate, and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0 N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention when administered intravenously at a rate of about 0.01 to 0.31 mg/kg/min caused dose related significant increases in cardiac contractility with only low or minimal changes in heart rate and moderate reduction in blood pressure. Thus the compounds of the present invention are also useful as antihypertensive agents.

Test Result of Preferred Compound N—[4-[2-(1,4,5,6-tetrahydro-4-methyl-6-oxo-3-pyridazinyl)-ethenyl]phenyl]-acetamide Using Anesthetized Dog Procedure

| Compound | Dose mg/kg | Percent Change | | |
|---|---|---|---|---|
| | | Myocardial Contractility | Heart Rate | Blood Pressure |
| Example 1 | 0.001 | 5 | — | −1 |
| | 0.003 | 14 | 1 | −16 |
| | 0.01 | 33 | 5 | −20 |
| | 0.03 | 56 | 7 | −19 |
| | 0.1 | 109 | 13 | −25 |

Accordingly the present invention also includes a pharmaceutical composition for increasing cardiac contractility and/or treating hypertension comprising an effective amount of a compound of the Formula I as defined above together with a pharmaceutically acceptable carrier.

The present invention further includes a method for increasing cardiac contractility and/or treating hypertension in mammals suffering therefrom comprising administering to such mammals either orally or parenterally a corresponding pharmaceutical composition containing a compound of the Formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.03 to 100 mg/kg of body weight per day or preferably 0.1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

N-[4-[2-(1,4,5,6-tetrahydro-4-methyl-6-oxo-3-pyridazinyl)ethenyl]phenyl]acetamide A solution of 8.2 g (0.05 mol) of 4-acetamidobenzaldehyde, 7.2 g (0.055 mol) of β-methyl levulinic acid, 6.3 g (0.075 mol) of piperidine in a mixture of 125 ml of toluene and 75 ml of tetrahydrofuran is heated under relux with a Dean Stark apparatus for two hours. The solution is evaporated under vacuo and the residue is taken up with dilute aqueous $K_2CO_3$ solution. The insoluble material is extracted with ether and discarded. The pH of the solution is adjusted to 5.6 and the gummy material is extracted with ethyl acetate. The extract is washed with saturated sodium chloride solution, dried, and evaporated. The residue is crystallized from 2-propanol to give 7.1 g of 6-[4(acetylamino) phenyl]-3-methyl-4-oxo-5-hexenoic acid, mp 189°–190° C.

Anal. Calcd for $C_{15}H_{17}NO_4$; C, 65.44; H, 6.22; N, 5.09; Found: C, 65.28, H, 6.25; N, 5.00. Hydrazine hydrate (0.9 g, 0.018 mol) is added to a solution of 3.3 g (0.012 mol) of the above acid in 30 ml of 85% acetic acid with cooling and the mixture is stirred overnight at room temperature. The reaction mixture is evaporated under vacuo and the residue is treated with dilute $K_2CO_3$ solution. The product was extracted with ethyl acetate and the extract is washed with water, dried, and evaporated to give a gummy solid. This is crystallized from ethanol to give 1 g of the product. mp 206°–207° C.

Anal. Calcd for $C_{15}H_{17}N_3O_2$; C, 66.40; H, 6.32; N, 15.49; Found: C, 66.70, H, 6.27; N, 15.43.

EXAMPLE 2

N-[4-[2-(1,4,5,6-tetrahydro-5,5-dimethyl-6-oxo-3-pyridazinyl)ethenyl]phenyl]acetamide By substituting α,α-dimethyl levulinic acid for β-methyl levulinic acid and following the procedure of Example 1, the above product is obtained, mp 255°–257° C.

Anal. Calcd for $C_{16}H_{19}N_3O_2$; C, 67.34; H, 6.71; N, 14.73; Found: C, 67.17; H, 6.70; N, 14.51.

I claim:

1. A compound of the formula

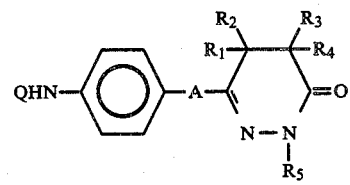

wherein Q is H or $COR_6$ wherein $R_6$ is lower alkyl of from one to four carbons inclusive or aryl; $R_1$, $R_2$, $R_3$, $R_4$, and $R_5$ are each independently hydrogen, lower alkyl or $R_2$ and $R_3$ when taken together may form a single bond such that a double bond is formed between the carbons to which $R_2$ and $R_3$ are attached; A is alkylene of one to four carbon atoms or alkenylene of two to four carbon atoms; or a pharmaceutically acceptable acid addition salt thereof.

2. A compound as claimed in claim 1, wherein $R_1$, $R_2$, $R_3$, $R_4$, and $R_5$ are each independently hydrogen or methyl and A is ethenyl.

3. A compound as claimed in claim 2, wherein Q is acetyl.

4. A compound as claimed in claim 3, and being N-[4-[2-(1,4,5,6-tetrahydro-4-methyl-6-oxo-3-pyridazinyl)ethenyl]phenyl]acetamide.

5. A compound as claimed in claim 1, and being N-[4-[2-(1,4,5,6-tetrahydro-5,5-dimethyl-6-oxo-3-pyridazinyl)ethenyl]phenyl]acetamide.

6. A pharmaceutical composition for increasing cardiac contractility, treating thrombosis, or lowering blood pressure comprising a cardiotonic, antithrombotic, or hypotensive effective amount of a compound as claimed in claim 1 together with a pharmaceutically acceptable carrier.

7. A method for increasing cardiac contractility in mammals in need thereof which comprises administering to such mammal an amount, effective to increase cardiac contractility, of a composition as claimed in claim 6.

8. A method for lowering blood pressure in a mammal suffering from hypertension which comprises administering to said mammal an antihypertensive effective amount of a composition as claimed in claim 6.

9. A method for treating thrombosis in a mammal suffering therefrom which comprises administering to said mammal an antithrombotically effective amount of a composition as claimed in claim 6.

* * * * *